ns as critical metal components molybdenum, bismuth and at least one transition metal selected from iron, nickel and cobalt, said catalyst being prepared by adding ammonium rhodanide to all or some of the starting liquid mixtures containing said catalytic metal components.

United States Patent [19]
Kubo et al.

[11] 3,980,709
[45] Sept. 14, 1976

[54] CATALYST FOR PREPARATION OF $\alpha,\beta$-UNSATURATED ALDEHYDES AND PROCESS FOR PREPARING THE ALDEHYDES

[75] Inventors: Masayoshi Kubo; Kazuyuki Matsuoka, both of Saitama, Japan

[73] Assignee: Daicel, Ltd., Osaka, Japan

[22] Filed: Dec. 9, 1974

[21] Appl. No.: 530,747

[30] Foreign Application Priority Data
Dec. 11, 1973    Japan.............................. 48-139335

[52] U.S. Cl............................ 260/604 R; 252/470
[51] Int. Cl.².................... B01J 23/78; C07C 45/04
[58] Field of Search.......................... 252/464, 470; 260/604 R

[56] References Cited
UNITED STATES PATENTS

| | | | |
|---|---|---|---|
| 3,171,859 | 3/1965 | Sennewald et al.............. | 252/470 X |
| 3,642,930 | 2/1972 | Grasselli et al..................... | 252/464 |
| 3,778,386 | 12/1973 | Takenaka et al................... | 252/470 |
| 3,786,000 | 1/1974 | Ono et al......................... | 252/470 X |
| 3,804,903 | 4/1974 | Hagiwara........................ | 260/604 R |

*Primary Examiner*—W. J. Shine
*Attorney, Agent, or Firm*—Woodhams, Blanchard and Flynn

[57] ABSTRACT

A catalyst for preparing $\alpha,\beta$-unsaturated aldehydes by the gas phase catalytic oxidation of $\alpha,\beta$-unsaturated hydrocarbons, comprising as critical metal components molybdenum, bismuth and at least one transition metal selected from iron, nickel and cobalt, said catalyst being prepared by adding ammonium rhodanide to all or some of the starting liquid mixtures containing said catalytic metal components.

6 Claims, No Drawings

CATALYST FOR PREPARATION OF α,β-UNSATURATED ALDEHYDES AND PROCESS FOR PREPARING THE ALDEHYDES

BACKGROUND OF THE INVENTION

1. Field of the Invention

This invention relates to the preparation of α,β-unsaturated aldehydes. More particularly, this invention relates to a method for preparing a catalyst characterized in that ammonium rhodanide is added during the stage of preparing the catalyst. Especially, this invention provides a catalyst having an enhanced activity for producing α,β-unsaturated aldehydes by the gas phase catalytic oxidation of α,β-unsaturated hydrocarbons.

2. Description of the Prior Art

Metal oxide catalysts comprising as main metal components molybdenum, bismuth and a transition metal, especially iron, cobalt or nickel, optionally containing other elements incorporated according to need, have heretofore been used as catalysts for the gas phase catalytic oxidation of α,β-unsaturated hydrocarbons. However, the known catalysts of this type have various disadvantages.

For example, the catalyst disclosed in Japanese Patent Publication No. 4771/69 (oxide catalyst of the Mo-Bi-Fe-As system) and the catalyst disclosed in Japanese Patent Publication No. 6246/69 (oxide catalyst of the Mo-Bi-Co-Ni-Fe-As system) include a poisonous substance such as arsenic oxide as a component which is effective for obtaining the desired acrolein product in a high yield. Accordingly, when these catalysts are employed, there is a danger that poisonous substances such as arsenic will be discharged outside the reaction system, depending on the working conditions or the working procedures. Further, since arsenic compounds have a very high toxicity, such operations as the preparing of an arsenic compound-containing catalyst, charging of such catalyst into a reaction vessel and withdrawal of the catalyst from a reaction vessel are very dangerous. Therefore, the method for preparing acrolein on an industrial scale by using a catalyst containing a poisonous substance such as an arsenic compound cannot be regarded as being an optimum method for industrial usage.

When oxides of Mo, Bi and Fe are used as main components of such a catalyst, there is generally adopted a catalyst-preparing method comprising dissolving ammonium molybdate in water, forming a nitric acid-acidified aqueous solution of ferric nitrate and bismuth nitrate, mixing both the solutions, adding a suitable carrier and other salts to the mixture according to need and performing the concentration, drying, molding and calcination steps. However, an oxide catalyst of the MoBi-Fe system prepared by this method possesses a much lower activity than an oxide catalyst of the Mo-Bi-Fe-As system, and it is not an advantageous catalyst for preparing acrolein economically. Further, during the preparation of this catalyst, molybdenum reacts with iron to form a gel-like precipitate and a good dispersion state of the metals cannot be obtained. Accordingly, it is difficult to obtain good reproducible results of catalytic activity when separate batches of catalyst are prepared. For these reasons, the use of arsenic in the oxide catalyst of this type is advantageous in terms of yield, but the use of arsenic is not preferred for the reasons set forth above.

SUMMARY OF THE INVENTION

We have discovered that unique catalysts of the molybdenum-bismuth-transition metal type, useful for the preparation of α,β-unsaturated carbonyl compounds and possessing economic and technological advantages, are obtained by adding ammonium rhodanide during the catalyst preparation stage. The resulting catalyst has a highly enhanced catalytic activity.

The role of arsenic in an oxide catalyst of the As-Mo-Bi-Fe system has been investigated with a view to overcoming the above-mentioned disadvantages brought about by the presence of the arsenic component. As a result, we discovered that if ammonium rhodanide is added during the catalyst preparation stage, instead of arsenic, a catalyst having a high activity to the gas phase catalytic oxidation of olefins can be obtained.

According to this invention, this highly active catalyst is prepared in the following manner.

Ammonium molybdate is dissolved in water and ammonium rhodanide is added thereto and is completely dissolved therein. Separately, iron nitrate and bismuth nitrate are dissolved in an aqueous solution acidified with nitric acid to a pH in the range of below 6. The acidified solution is mixed with the above aqueous solution of ammonium molybdate. If needed, an inert catalyst carrier is added to the mixture. Then, the mixture is concentrated and dried by heating in air at a temperature below 200°C. The resulting dried product is treated in an air current at a temperature in the range of 200° to 400°C to decompose the nitrates, and then it is molded and calcined, at a temperature in the range of 400° to 700°C, to obtain a final catalyst. Effective catalysts, according to the invention, can be obtained if ammonium rhodanide is added to the aqueous solution of ammonium molybdate or if it is added to the nitric acid-acidified aqueous solution of iron nitrate and bismuth nitrate. Further, the same improved effects can be obtained by adding ammonium rhodanide during the preparation of catalysts containing, in addition to Mo, Bi and Fe, elements of Groups I, III, V and VI of the Periodic Table, such as K, Rb, Cs, W, P and B. Accordingly, the catalysts to which this invention can be applied are not limited to oxide catalysts of the Mo-Bi-Fe system.

Furthermore, another interesting discovery is that in the case of catalysts of the Mo-Bi-Fe (or Ni or Co)-As system, if ammonium rhodanide is added during the catalyst preparation stage, the catalytic activity of such arsenic-containing catalyst also can be significantly increased. In view of the foregoing discoveries, it is concluded that ammonium rhodanide contributes greatly to improvement of the catalytic activity.

As pointed above, the initial discovery resided in using ammonium rhodanide as a substitute for an arsenic compound. But as a result of further study it was found that even in the case of a catalyst of the Mo-Bi-Fe (or Co or Ni)-As system containing an arsenic compound as one catalyst component, the catalytic activity can also be improved by addition of ammonium rhodanide. Accordingly, this invention is of broad applicability to catalysts containing molybdenum, bismuth and transition metal, as essential metal components, and optionally containing various other metals, and used for the preparation of α,β-unsaturated aldehydes. The catalyst has a high activity of great value from the practical viewpoint, whether or not it contains an arsenic compound as one component.

More specifically, in accordance with this invention, there is provided a catalyst for preparing α,β-unsaturated aldehydes by the gas phase catalytic oxidation of α,β-unsaturated hydrocarbons, comprising as critical metal components molybdenum, bismuth and at least one transition metal selected from iron, nickel and cobalt, said catalyst being prepared by adding ammonium rhodanide to all or some of starting liquid mixtures containing said catalytic metal components.

According to this invention, the yields of α,β-unsaturated aldehydes such as acrolein can be highly improved by incorporating ammonium rhodanide in an otherwise known catalyst system. Even if a poisonous compound such as an arsenic compound, is not present in the catalyst, a sufficiently high activity can be obtained.

The amount of ammonium rhodanide added during the catalyst preparation stage is in the range of from 0.1 to 10 percent by weight, preferably 0.5 to 5 percent by weight, based on the metal content of the final catalyst composition.

Conventional inert catalyst carriers such as silica, silica-alumina, diatomaceous earth and pumice can be, and preferably are employed in the above-mentioned catalyst composition of this invention.

The amounts of the metals in the catalyst are not particularly critical in this invention. There can be used any known metal oxide catalyst compositions useful for the catalytic gas phase oxidation of α,β-olefinically unsaturated hydrocarbons to form α,β-olefinically unsaturated aldehydes. For example, there can be used a metal oxide catalyst, the metal content of which is expressed by the following empirical formula $$(Mo)_a(Bi)_b(J)_c(L)_d(O)_e$$

wherein J is Fe, Co, Ni or mixtures thereof, L is one or more metals selected from the metals of Groups I (alkali metal), III, V and VI of the Periodic Table, and $a$, $b$, $c$, $d$ and $e$ represent the number of atoms of Mo, Bi, J, L and O, respectively $a$ being 12, $b$ being from 0.5 to 6, $c$ being from 3 to 12, $d$ being from 0 to 10 and $e$ being the number of oxygen atoms sufficient to satisfy the atomic valences of Mo, Bi, J and L. Such catalysts are known in the art. The catalyst of this invention exhibits the above-mentioned catalytic activity when it is used for preparing α,β-unsaturated aldehydes by catalytically oxidizing α,β-unsaturated hydrocarbons in the gas phase with molecular oxygen, especially preferably for oxidizing propylene and isobutylene to corresponding unsaturated aldehyde compounds such as acrolein and methacrolein, respectively. When the catalyst of this invention is used for such oxidation, acrolein and other α,β-unsaturated aldehydes can be obtained in high yields. As is well known, the reaction is carried out in the gas phase, using a molecular-oxygen containing gas as an oxidizing agent, at a temperature of 250° to 400°C. Further details of this process are disclosed in U.S. Ser. No. 376 317, filed July 5, 1973, now U.S Pat. No. 3,894,091.

This invention will now be described in more detail by reference to the following illustrative Examples.

EXAMPLE 1

18.68 g of ammonium molybdate [$(NH_4)_6Mo_7O_{24}\cdot 4H_2O$] and 0.67 g of ammonium rhodanide ($NH_4SCN$) were dissolved with heating in 200 ml of water. Separately, 26.72 g of ferric nitrate [$Fe(NO_3)_3\cdot 9H_2O$], 8.56 g of bismuth nitrate [$Bi(NO_3)_3\cdot 5H_2O$] and 0.35 g of potassium nitrate ($KNO_3$) were dissolved under heating into 23 ml of a nitric acid-acidified aqueous solution. The acidified solution was mixed with the above ammonium molybdate solution. Then, 50 g of silica gel having a size of 150 mesh (Japanese Industrial Standard), or smaller, was added to the mixture, and the mixture was concentrated under agitation and heating to form a slurry. The catalyst slurry was dried in air maintained at 120°C., then heated at 350°C. to decompose the metal salts, cooled and pulverized. The pulverized product was molded into cylindrical pellets (having a diameter of 5 mm and a length of 3mm), and the molded pellets were calcined in an air current at 560°C. for 4 hours. The resulting metal oxide catalyst had a metal element atomic ratio expressed as $Mo_{12}Fe_{7.5}Bi_2K_{0.4}$.

A stainless steel U-shaped tube having an inner diameter of 27 mm was packed with 60 m of the thus-obtained catalyst and was immersed in a molten salt bath consisting of 3% $NaNO_3$, 50% $KNO_3$ and 47% $NaNO_2$ by weight, and a gas mixture comprising 6 mole % of propylene and 42.8 mole % of air with the balance being steam was passed through the tube at a reaction temperature of 340°C. so that the contact time was 2.4 seconds.

The obtained results are as follows:
Conversion of propylene : 93.8 mole %
Yield of Acrolein : 74.1 mole %
Selectivity to acrolein : 79.0 mole %

COMPARATIVE EXAMPLE 1

18.68 g of ammonium molybdate [$(NH_4)_6Mo_7O_{24}\cdot 4H_2O$] was dissolved under heating in 200 ml of water. Separately, 26.72 g of ferric nitrate [$Fe(NO_3)_3\cdot 9H_2O$], 8.56 g of bismuth nitrate [$Bi(NO_3)_3\cdot 5H_2O$] and 0.35 g of potassium nitrate [$KNO_3$] were dissolved under heating in 23 ml of a nitric acid-acidified aqueous solution, and the solution was mixed with the above ammonium molybdate solution. Post treatments were conducted in the same manner as described in Example 1 to obtain pellets having a diameter of 5 mm and a length of 3 mm.

The metal element atomic ratio in the thus-obtained metal oxide catalyst is expressed as $Mo_{12}Fe_{7.5}Bi_2K_{0.4}$. The gas phase catalytic oxidation of propylene was conducted by using the thusobtained catalyst while employing the same gas composition and reaction conditions as in Example 1.

The conversion of propylene was 86.6 mole %, the yield of acrolein was 66.5 mole % and the selectivity to acrolein was 76.8 mole %. Further, carbon dioxide gas, carbon monoxide and organic acids were formed as by-products.

When the reaction results of Example 1 are compared with those of Comparative Example 1, it will readily be understood that a catalyst of the Mo-Fe-Bi-K system can be highly activated by addition of ammonium rhodanide and the acrolein-producing activity is much improved over the case were ammonium rhodanide is not added.

The embodiments of the invention in which an exclusive property or privilege is claimed are defined as follows:

1. In a catalyst composition consisting essentially of oxides of elements as active catalyst constituents, wherein said elements comprise molybdenum, bismuth, at least one transition metal selected from the group consisting of iron, nickel and cobalt, and potassium, said catalyst composition being prepared by mixing aqueous solutions of water-soluble salts of said elements, and then drying the mixture to obtain the solids and calcining the solids to obtain the catalyst composition, the improvement which comprises: said catalyst composition is prepared by incorporating ammonium rhodanide into at least one of said aqueous solutions.

2. A catalyst composition as claimed in claim 1, in which said catalyst composition is deposited on particles of an inert catalyst carrier.

3. A process for preparing a catalyst composition consisting essentially of metal oxides as active catalyst constituents, wherein said metals comprise molybdenum, bismuth and at least one transition metal selected from the group consisting of iron, nickel and cobalt, which comprises mixing aqueous solutions of water-soluble salts of said metals, and then drying the mixture to obtain the solids and calcining the solids to obtain the metal oxide catalyst composition, the improvement which comprises: incorporating ammonium rhodanide in at least one of said aqueous solutions.

4. A process as claimed in claim 3, in which an aqueous solution of ammonium molybdate is mixed with an aqueous solution of ferric nitrate and bismuth nitrate.

5. A process as claimed in claim 3, in which an inert catalyst carrier is incorporated into the mixture of said aqueous solutions.

6. In a process for the preparation of acrolein or methacrolein by catalytically oxidizing propylene or isobutylene, respectively, in the gas phase, with a molecular oxygen-containing gas, at a temperature of 250° to 400°C, the improvement which comprises: conducting the reaction in the presence of the catalyst composition as claimed in claim 1.

* * * * *